United States Patent [19]

Gomes

[11] Patent Number: 5,636,984
[45] Date of Patent: Jun. 10, 1997

[54] DENTAL INSPECTION DEVICE

[75] Inventor: John Gomes, Singapore, Singapore

[73] Assignee: Atox Innovations Pte Ltd., Sinapore, Singapore

[21] Appl. No.: 325,469

[22] PCT Filed: Apr. 30, 1993

[86] PCT No.: PCT/GB93/00903

§ 371 Date: Jan. 3, 1995

§ 102(e) Date: Jan. 3, 1995

[87] PCT Pub. No.: WO93/21817

PCT Pub. Date: Nov. 11, 1993

[30] Foreign Application Priority Data

May 1, 1992 [GB] United Kingdom ............... 9209471

[51] Int. Cl.$^6$ ................................................ A61C 3/00
[52] U.S. Cl. ............................................................ 433/30
[58] Field of Search ............................. 433/29, 30, 31

[56] References Cited

U.S. PATENT DOCUMENTS

| | | | |
|---|---|---|---|
| 1,283,189 | 10/1918 | Houck | 433/31 X |
| 1,817,417 | 8/1931 | Weitzler | 433/31 X |
| 1,989,162 | 1/1935 | Barr | 433/31 |
| 4,219,331 | 8/1980 | Getz | 433/31 X |
| 4,872,838 | 10/1989 | Canter et al. | 433/31 |

FOREIGN PATENT DOCUMENTS

| | | | |
|---|---|---|---|
| 471421 | 9/1937 | United Kingdom | 433/31 |
| 8000300 | 3/1980 | WIPO | 433/31 |
| 8808686 | 11/1988 | WIPO | 433/31 |

*Primary Examiner*—Nicholas D. Lucchesi
*Attorney, Agent, or Firm*—Young & Basile, P.C.

[57] ABSTRACT

A spacer comprises a handle (2) which is extended according to a certain angle by a spatula-shaped flat part (3). A removable cap (4) made of hard, transparent plastic material, containing an electric bulb (5) and electric contacts (6), is plugged in the extremity of the spatula (3). The electric supply of the bulb (4), by operation of a switch (9), is provided by means of batteries (8) housed inside the handle (2). The cap (4) and the spatula (3) are housed into a sleeve (20) made of flexible transparent plastic material, and disposable after use. The apparatus is particularly usable for lowering and holding the tongue and as optical inspection instrument for dentists.

13 Claims, 4 Drawing Sheets

DENTAL INSPECTION DEVICE

FIELD OF THE INVENTION

The present invention relates to a dental inspection device, which is intended to allow an individual layman to conduct his own dental examination. It may also be used for veterinary examination or for general use in industry.

BACKGROUND OF THE INVENTION

Most people have at one time or another experienced difficulties in conducting a proper dental examination of their own teeth, for example by looking in a mirror. There is thus a danger of people neglecting to check their teeth regularly, particularly if periodical check-ups are not carried out by a dentist. In this way, irreparable dental damage may occur, which might have been prevented had a simple device been available with which the individual could regularly monitor his own teeth and gums.

U.S. Pat. No. 4,993,945 discloses a heated dental mirror which is battery operated and includes an illumination device. International patents WO80/00300 and WO88/08686 also disclose illuminated mirrors.

U.S. Pat. No. 4,872,838 discloses a complex self inspection device which includes extenders for moving the cheek out of the way. However the construction is complicated, expensive to produce and difficult to use.

It is an object of the present invention to provide a device of the aforementioned type which improves on those currently available.

SUMMARY OF THE INVENTION

Thus, the present invention provides a dental inspection device which comprises:

a handle portion, an illumination means, a mouth portion, and a neck portion connecting the mouth portion to the handle portion;

a low voltage battery means located in the handle portion, which is electrically connected to illumination means for illuminating the object to be viewed; and a mirror means located in the mouth portion for dental inspection, wherein;

the neck portion is at least as wide as the handle portion such as to displace the cheek or tongue of the person during viewing and to give an unobstructed view of the mirror means.

For ease of operation, the neck portion is preferably offset relative to the handle portion. However, the mirror means and the mouth portion are preferably substantially parallel to the handle portion.

In order to prevent condensation on the mirror means during use, the device may include a heater for heating the mirror means, and which is operated from the low voltage battery means. However, in a preferred embodiment the illumination means comprises an electric bulb and a metal reflector located behind the bulb. The mirror means is also formed of metal and is in heat-conductive connection with the metal reflector such that heat generated by the bulb heats the reflector, which in turn heats the mirror means. Preferably, the reflector and the mirror means are formed from a single piece of metal.

The handle portion preferably includes an end cover for the battery compartment which allows insertion of the battery means. For simplicity and ease of construction, the end cover is preferably rotatable and is provided with switch means for turning the illumination means (and preferably any heater used) on and off as the end cover is rotated.

The mirror means may be a magnifying, e.g. concave mirror, to facilitate viewing.

The illumination means may be located in a cavity adjacent the mirror means and be arranged for directing light onto the object being viewed. A convex lens may be located over the bulb and sealed to the periphery of the reflector, so as to enclose the bulb and protect it from dirt and saliva. The lens focusses light onto the object being viewed. Advantageously, a guard is provided adjacent the illumination means for shielding thereof to substantially prevent light shining directly into the users eyes.

In order to allow rinsing and sterilisation, the entire device is preferably water resistant and sealed against water entry.

DESCRIPTION OF PREFERRED EMBODIMENTS

Embodiments of the present invention will now be described by way of example only with reference to the drawings therein:

Figure 1:
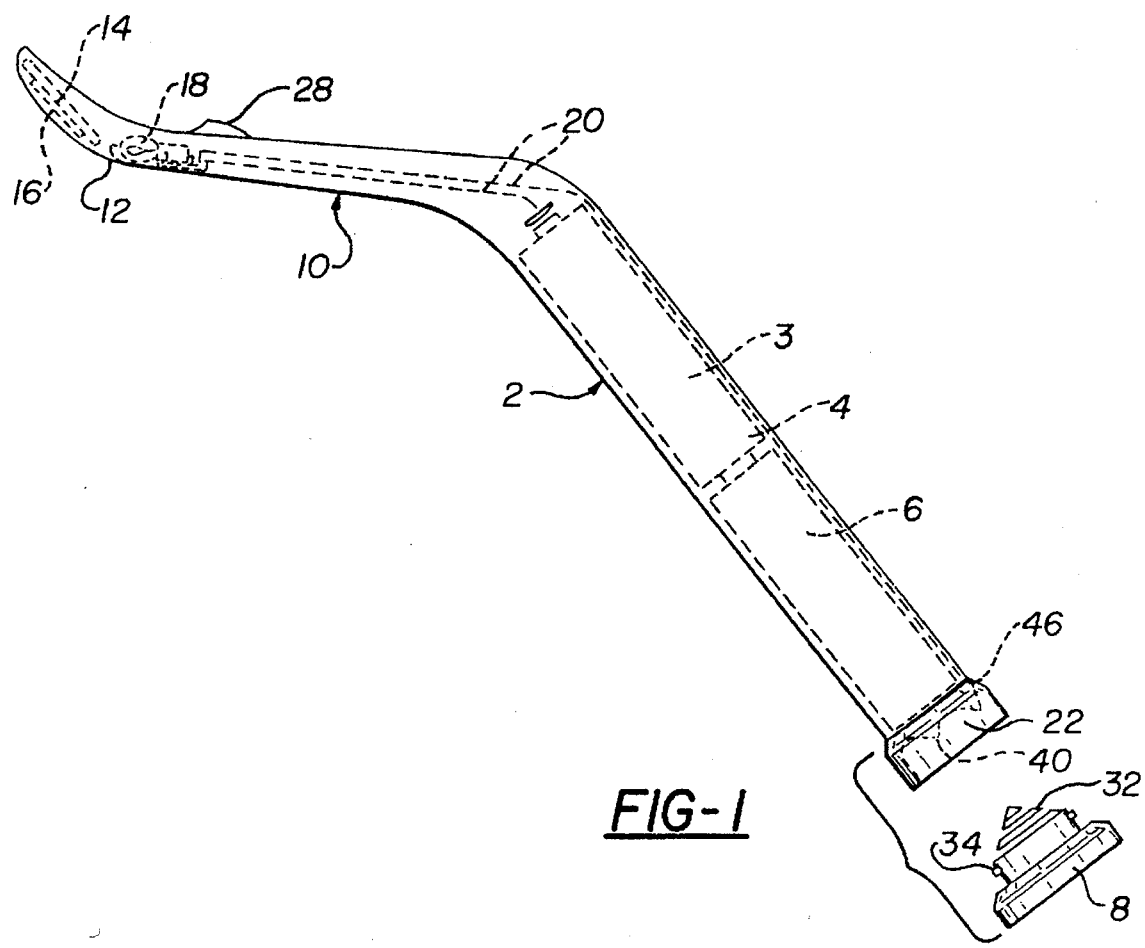
FIG. 1 is an exploded elevational view of a first embodiment of a dental inspection device.
Figure 2:
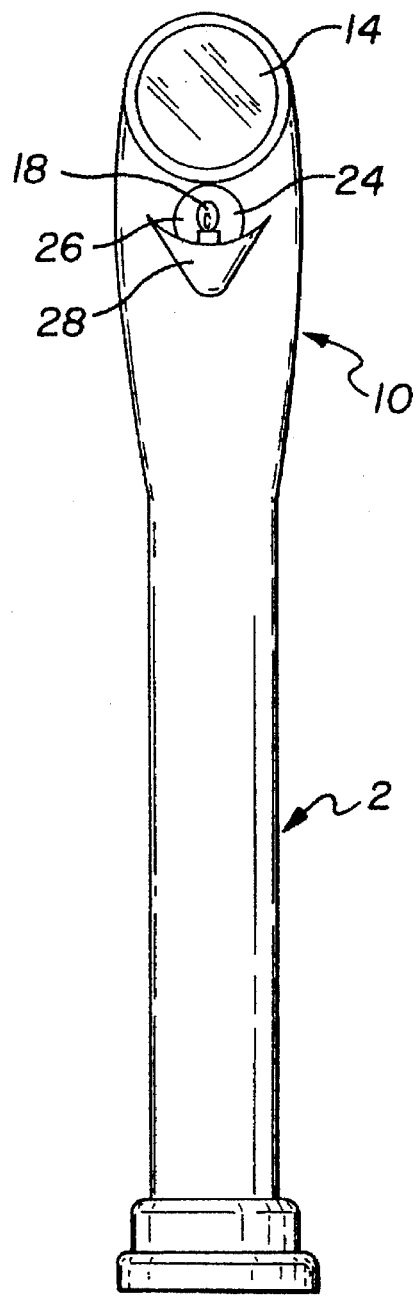
FIG. 2 is a front elevation.

The dental device shown in FIGS. 1 and 2 comprises a handle portion 2 containing two batteries 4, 6 and closed by an end cover 8. An offset neck portion 10 connects the handle portion to the mouth portion 12 in which is located a magnifying mirror 14. The mirror is heated by a heater 16 powered by the batteries.

A light bulb 18 is located in a cavity 24 and is connected to the batteries via leads 20 and on/off switch 22. The cavity includes a reflector 26. A shield 28 prevents light from shining directly into the users eyes and also protects the bulb from damage.

The neck portion 10 is wider than the handle portion 2 so as to push the cheek or tongue of the user to one side during inspection and to prevent the view of the mirror being obstructed.

Figure 5:
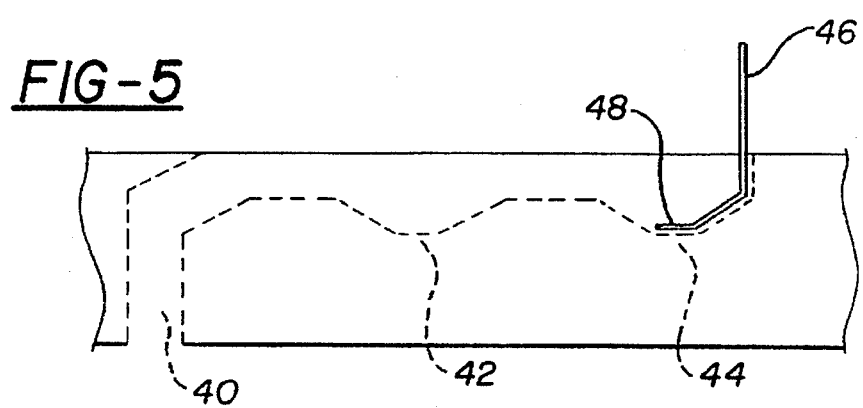
FIG. 5 is an opened flat view of a groove in the end of the battery compartment along which passes a flexible metal lever constituting the on/off switch.
Figure 3:
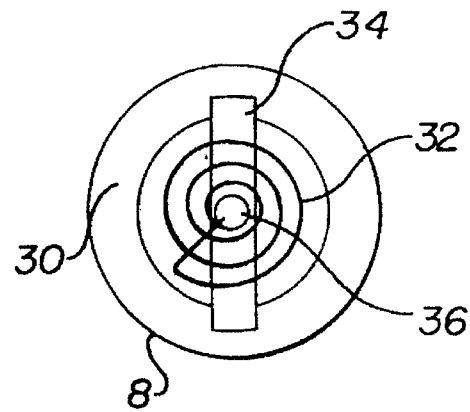
FIG. 3 is a view from above the battery compartment end cover.
Figure 4:
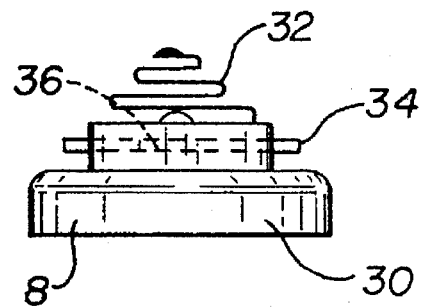
FIG. 4 is a side elevation of the end cover.

FIGS. 3, 4 and 5 show the end cap and on/off switch construction. The end cap 8 comprises a cover body 30, and a cone-shaped helical spring 32 and flexible metal lever 34 connected thereto by means of a screw 36. The apex of the spring 32 makes contact with the base of the battery 6 and is also in electrical contact with the flexible metal lever 34.

As shown in FIG. 5, this lever 34 during fitting and rotation of the end cover passes up a groove 40 in the wall of the open ended battery compartment 3 in the handle. Pushing the end cover in and rotating slightly retains the end cover in place with the lever in the first recessed position 42 in the groove. This is the "off" position of the heater and light. Further rotation of the end cover moves the lever 34 into the second recessed position 44 which contains the end contact 48 of contact 46 which is electrically connected to a lead 20. In this way, rotation of the end cover acts as an on/off switch, controlling live electric current from the batteries 4, 6 via the spring 32 and lever 34 to the terminal 46 and thence to the light bulb 18.

The dental inspection device is particularly convenient to use and can even be operated by a child. Since no assistance is required from anyone else, each individual can inspect his own teeth in the privacy of his own home as often as is required, without the expense and inconvenience of visiting a dentist.

Figure 6:
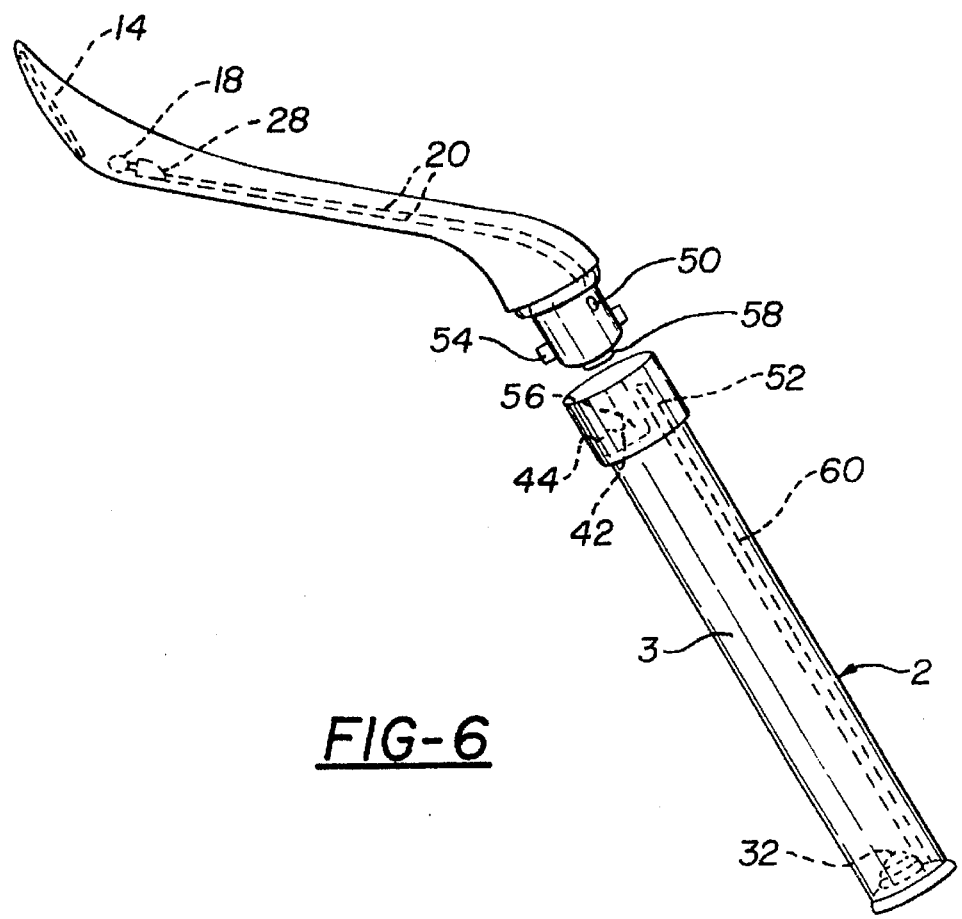
FIG. 6 is an elevation of a second embodiment.

A second embodiment is shown in FIG. 6 wherein the same reference numerals are used for analogous parts. It differs from the first embodiment in that the whole handle 2 is twisted to operate the on/off switch for the heater and light. The neck portion is attached to the handle by locking studs 54 which engage in a groove 56 on the handle. Contact 58 acts as the positive battery terminal, whilst contact 50 engages a negative contact 52 on metal strip 60 which in turn is in contact with the negative battery terminal 32.

Figure 7:
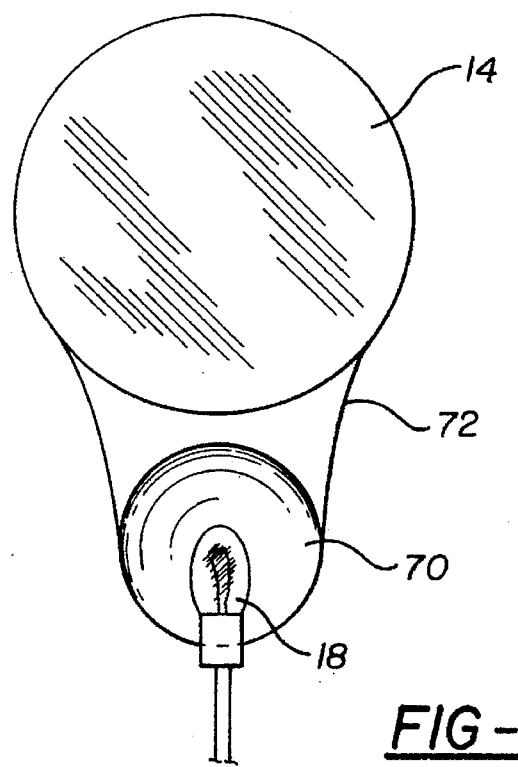
FIG. 7 shows the mirror and reflector formed from a single piece of metal, according to a third embodiment.
Figure 8:
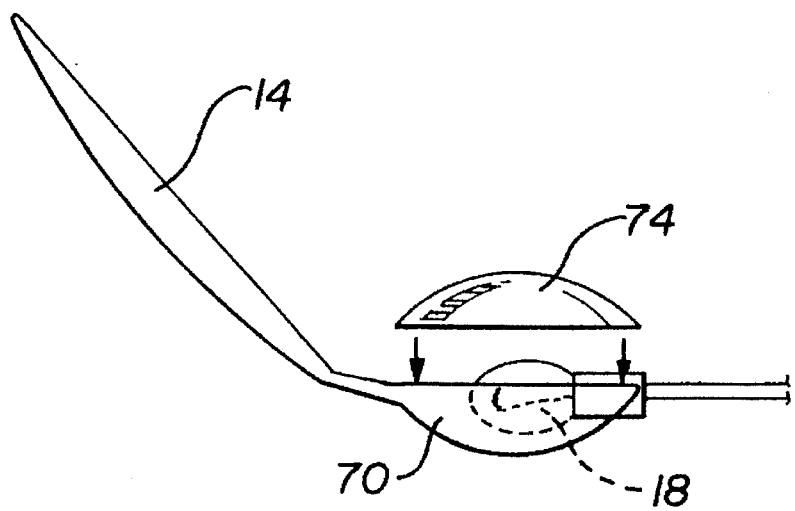
FIG. 8 shows a convex lens located over the bulb and reflector.
Figure 9:
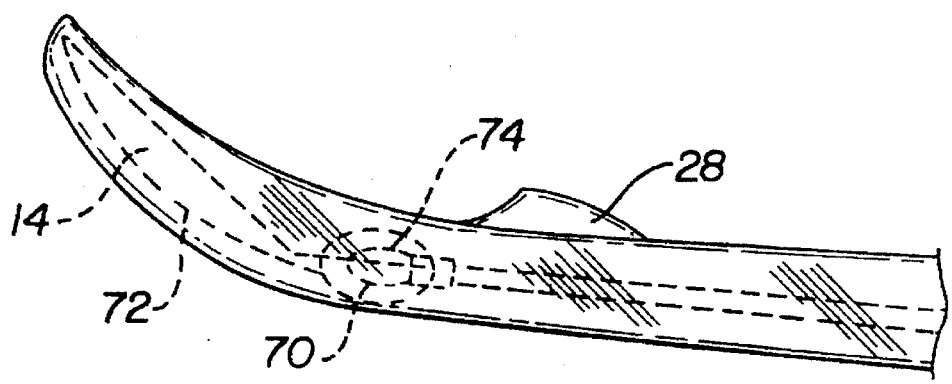
FIG. 9 is a general view of the head and neck of the third embodiment.

FIGS. 7, 8 and 9 shows a third embodiment wherein bulb 18 is located at the centre of a concave reflector 70. The reflector is formed from a single piece of metal 72 which also comprises the concave magnifying mirror 14. In this way, heat from the bulb is transmitted by conduction to the mirror and prevents the mirror from condensation.

As shown in FIG. 8, a convex acrylic lens 74 is fitted over the bulb 18 such as to seal around the periphery of the reflector 70. This protects the bulb from damage, and from dirt and saliva. The lens could be made of glass or other suitable material.

The various components of the device are made of heat resistant non-corrodable materials, such that the device (with batteries removed) can be sterilised in boiling water or in antiseptic solution. The use of a metallic mirror eliminates the danger of broken glass chips, which may arise from conventional glass mirrors. The simple design facilitates mass production.

I claim:

1. A single bodied dental inspection device for use on a person which comprises:

a longitudinally extending handle portion, an illumination means, a mouth portion, and a neck portion connecting the mouth portion to the handle portion;

a compartment for storing a low voltage battery located in the handle portion, and means for electrically connecting the battery to illumination means for illuminating the mouth; and a mirror means located in the mouth portion for dental inspection, wherein;

the neck portion is at least as wide as the handle portion such as to displace the cheek or tongue of the person during viewing and give an unobstructed view of the mirror means.

2. A device according to claim 1 wherein the neck portion is offset relative to the handle portion.

3. A device according to claim 2 wherein the mirror means and the mouth portion are substantially parallel to the handle portion.

4. A device according to claim 1 wherein the illumination means comprises a bulb and a reflector, the reflector and the mirror means being formed of metal such that heat from the bulb is conducted to warm the mirror means and prevent condensation thereon.

5. A device according to claim 4 which further comprises a convex lens over the bulb and fitted to the periphery of the reflector to protect the bulb.

6. The device according to claim 4, wherein the reflector is formed from a single metal piece including a concave magnifying mirror.

7. The device according to claim 1, wherein the mirror means is a single metallic concave magnifying mirror.

8. The device according to claim 1, wherein the device is made of heat resistant and non-corrodible material.

9. A dental inspection device for use on a person which comprises:

a longitudinally extending handle portion, an illumination means, a mouth portion, and a neck portion connecting the mouth portion to the handle portion;

a compartment for storing a low voltage battery located in the handle portion, and means for electrically connecting the battery to illumination means for illuminating the mouth; and a mirror means located in the mouth portion for dental inspection, wherein;

the neck portion is at least as wide as the handle portion such as to displace the cheek or tongue of the person during viewing and give an unobstructed view of the mirror means wherein the handle portion includes an end cover for the compartment which allows insertion of the battery, the end cover being rotatable and being provided with switch means for turning the illumination means on and off.

10. A device according to claim 9 wherein the mirror means is a magnifying mirror.

11. A device according to claim 10 wherein the illumination means is located in a cavity adjacent the mirror means for directing light onto the object being viewed.

12. A device according to claim 10 which further comprises a guard adjacent the illumination means for shielding thereof to substantially prevent light shining directly into the user's eyes.

13. A device according to claim 9 which is sealed against liquid entry.

* * * * *